(12) United States Patent
Roberts et al.

(10) Patent No.: US 8,463,405 B2
(45) Date of Patent: Jun. 11, 2013

(54) ELECTRIC- OR MAGNETIC-FIELD BASED DETECTION OF WHEN ELECTRODE PADS HAVE BEEN HANDLED OR REMOVED FROM THEIR PACKAGE

(75) Inventors: Douglas Roberts, Bellevue, WA (US); Kim Hansen, Renton, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1957 days.

(21) Appl. No.: 10/561,334

(22) PCT Filed: Jun. 1, 2004

(86) PCT No.: PCT/IB2004/001967
§ 371 (c)(1),
(2), (4) Date: Dec. 15, 2005

(87) PCT Pub. No.: WO2005/000393
PCT Pub. Date: Jan. 6, 2005

(65) Prior Publication Data
US 2008/0140171 A1    Jun. 12, 2008

Related U.S. Application Data

(60) Provisional application No. 60/483,198, filed on Jun. 27, 2003.

(51) Int. Cl.
*A61N 1/3925* (2006.01)
(52) U.S. Cl.
USPC ........................................... 607/142

(58) Field of Classification Search
USPC ...... 607/1, 5, 14, 142; 128/640, 696; 206/328
See application file for complete search history.

(56) References Cited

U.S. PATENT DOCUMENTS

| | | | |
|---|---|---|---|
| 4,165,749 A * | 8/1979 | Cansell | 607/5 |
| 4,785,812 A * | 11/1988 | Pihl et al. | 607/8 |
| 5,645,571 A | 7/1997 | Gilman et al. | |
| 5,700,281 A * | 12/1997 | Brewer et al. | 607/5 |
| 6,083,246 A | 7/2000 | Stendahl et al. | |
| 6,292,697 B1 | 9/2001 | Roberts | |
| 6,336,047 B1 * | 1/2002 | Thu et al. | 607/5 |
| 2003/0055478 A1 * | 3/2003 | Lyster et al. | 607/142 |

FOREIGN PATENT DOCUMENTS

| EP | 57561 B | * | 4/1986 |
| EP | 57561 B | * | 4/1986 |

* cited by examiner

*Primary Examiner* — Christopher D Koharski
*Assistant Examiner* — Jeremiah Kimball (57) ABSTRACT

Handling or removal of a pair of defibrillator electrode pads from their package is detected in order to effectively time the issuance of prompts to guide the user. One plate of a capacitor is embedded in the package, the electrode pads and lead wires serving as the other plate. Impedance across the capacitor in an alternating current circuit is monitored to detect an increase in the distance between the pads and the package. The impedance level is determined, in a low-cost hardware solution, by rectifying and then integrating an output voltage of the capacitor to produce a voltage signal whose magnitude attenuates as the pads are handled or removed. In one embodiment, the above methodology is time-division multiplexed with an alternative process that identifies handling or removal based on pad-to-pad impedance. In a further embodiment, the capacitive configuration is replaced with an inductive one.

20 Claims, 5 Drawing Sheets

ELECTRIC- OR MAGNETIC-FIELD BASED DETECTION OF WHEN ELECTRODE PADS HAVE BEEN HANDLED OR REMOVED FROM THEIR PACKAGE

CROSS REFERENCE TO RELATED APPLICATION

This application claims the benefit of U.S. provisional application Ser. No. 60/483,198 filed Jun. 27, 2003, which is incorporated herein.

BACKGROUND OF THE INVENTION

1. Field of the Invention

The present invention relates to electrodes, and, more particularly, to detecting movement of electrodes.

2. Discussion of the Prior Art

In the US alone, over 350,000 people die annually from Sudden Cardiac Arrest. Many of these victims have no prior warning of heart disease, and 70% die outside the hospital. The only treatment for an SCA victim is to provide an immediate, high-energy electric shock through the heart. Minimizing the time to first shock is critical since, for every minute after 4 minutes, the chances of resuscitation decrease by 10%. If a shock is not applied within 10 minutes, the chances of resuscitation are almost zero.

U.S. Pat. No. 5,700,281, issued on Dec. 23, 1997, hereinafter "the '281 patent," the entire disclosure of which is incorporated herein by reference, discloses the use of prompts to guide a user in assisting an SCA victim. The '281 patent uses impedance values between the electrode pads to determine the stage of a rescue attempt in order to prompt and thereby guide the user. Yet, guidance for the deployment and application of the electrode pads in a timely manner is not available.

SUMMARY OF THE INVENTION

In an effort to save as many as possible of the 350,000 lives per year lost to SCA, Automated External Defibrillators, or AEDs, are being placed where people live, work, travel and play. The objective is to provide the tool that can be used by a minimally trained or untrained witness to administer these lifesaving shocks as quickly as possible.

Because the witnesses are not usually trained in the use of defibrillators, AEDs must not only interpret the heart rhythm to determine if a shock is required, but they must also guide the users through the process of calling Emergency Medical Systems, removing the clothes from the patient's chest, removing the pads from their sealed package, and applying these pads to the correct location on the patient's chest. Different users complete these steps at different paces. For example, removing the clothes to bare the patient's chest might be a quick process if the patient is only wearing a tee-shirt, but will take much longer if there are multiple layers that need removing or cutting away.

In order to minimize confusion during an already anxious event, the AED should not begin to give the voice prompts for the next action, like applying the pads to the patient's bare chest, until the current action, i.e. removing the clothes, has been completed. The challenge lies in how the AED detects when the current action has been completed.

Some AEDs require the user to press a button when the current action has been completed. This is a clean method of advancing the prompts, but breaks down if the user fails to press the button. If the button is not pressed, the voice prompts do not proceed and precious time is lost while the user tries to determine the cause of the delay.

Some AEDs include only minimal, more generalized prompts, which do not need to be advanced. However, these prompts do not guide the user step-by-step through the process, and may not be sufficient to help a confused user. Again, precious time may be lost.

Some AEDs may advance their prompts after a certain amount of time, regardless of whether the user has completed the current action or not. This can create confusion and anxiety for the user if the current step has not yet been completed, or if the current step is completed quickly.

As mentioned previously, correct and timely pad placement is essential to the efficacy of the shock. By sensing that the pads are being physically handled and manipulated by the user, the AED can determine that the previous action of calling 911 and removing the clothes has been completed. In this way, with no further button presses required of the user, the AED will immediately cease repeating its "Remove all clothes from the patient's chest" prompt and begin repeating the new prompt, "Look carefully at the pictures on the first pad. Remove the pad from the release liner and apply it exactly as shown in the picture." This invention allows the AED to advance to the next prompt when, and only when the user is ready to progress to the next step, without additional input from the user.

Advantageously, the present invention provides a solution to accurately advance the voice prompts between two very critical actions: removing the clothes from the patient's chest and applying the pads to the patient's chest.

One methodology for achieving this objective is disclosed in commonly owned, pending patent application, entitled "METHOD FOR DETECTING WHEN ELECTRODE PADS HAVE BEEN HANDLED OR REMOVED FROM THEIR PACKAGE", filed on Jun. 27, 2003, hereinafter cited as the '674 application, the entire disclosure of which is incorporated by reference herein. In the '674 application, the pad-to-pad impedance of pre-connected electrode pads is continuously monitored from the moment the AED has been turned on, or from a certain time after the device has been turned on, watching for changes or variability in this impedance measurement. Pre-connected electrode pads are pads that have been electrically attached to the defibrillator prior to the moment of need. In this way, the pads are ready for immediate deployment. In addition, if these pre-connected pads are electrically connected to each other, the AED can measure the impedance between the pads.

A high-impedance pad-to-pad connection is described in pending, commonly-owned US Patent Publication 2003/0055478, entitled "Medical Electrode and Release Liner Configuration Facilitating Packaged Electrode Characterization," filed on Sep. 14, 2001, hereinafter "the '478 publication," the entire disclosure of which is incorporated herein by reference.

The pad-to-pad impedance level is fairly constant while the pre-connected pads are sealed untouched inside their package which hereinafter is intended to refer to any type of container, such as a rigid sealed tray or a flexible sealed film package, or combination of both. However, when a user opens the pads' package and pulls out the pads, the pad-to-pad impedance changes due to the physical manipulation, handling and bending of the pads. If the magnitudes of these impedance changes are great enough, over the existing noise floor, the AED will detect them and determine that the pads state is being changed: from being sealed in their package to being handled or removed from their package.

Removal of the electrodes from their package can, however, be sufficiently slow, gentle or gradual that the event cannot reliably be identified based-on pad-to-pad impedance variation, because the disturbance or flexing of the pad does not meet the threshold needed for detection.

The present invention is directed to an alternative or additional method for detecting the handling or removal of electrode pads from their package that functions effectively no matter how slowly or gently the pads are handled or removed, because the present method detects the event of pad handling/removal based on the distance between the pads including their lead wires and a conductor embedded within the package. By means of an alternating current, an electric field is established between the conductor, as one plate of a capacitor, and the pads and wires as the other plate of the capacitor. Distance between the capacitor plates is sensed to determine when the pads have been handled or removed. Advantageously, the hardware for implementation is low in cost.

In accordance with the present invention, the handling/removal of an electrode and an attached wire is detected by an apparatus that includes, in addition to the electrode and lead wire a conductor, a source of alternating current (AC), and an electrode deployment detector. The apparatus monitors a magnitude of an electrical characteristic measured from an electrical circuit having from the AC source an alternating electric current path that includes the electrode with attached lead wire, the conductor and a space or other electrical insulator intervening between the conductor and the electrode with attached lead wire. The conductor is disposed in proximity of the electrode with attached lead wire to create capacitance in the electrical circuit. The electrode deployment detector is configured for identifying, based on the magnitude, the handling of the electrode with attached lead wire or the removing of the electrode with attached lead wire from a package containing the electrode with attached lead wire.

According to another aspect, the present invention includes an apparatus having an alternating current (AC) source and an AC circuit powered by the source and having a complex-impedance-generating element. The element has at least one electrode pad within the circuit, and is expandable from a package containing the element to change a voltage drop across the element. Further included in the apparatus is an electrode deployment detector for monitoring a magnitude of an electrical characteristic measured from the circuit. Based on said magnitude, handling of the element and removing of the element from the package is identified.

BRIEF DESCRIPTION OF THE DRAWINGS

Details of the invention disclosed herein shall be described with the aid of the figures listed below, wherein like features are numbered identically throughout the several views.

DETAILED DESCRIPTION OF THE PREFERRED EMBODIMENTS

Figure 1:
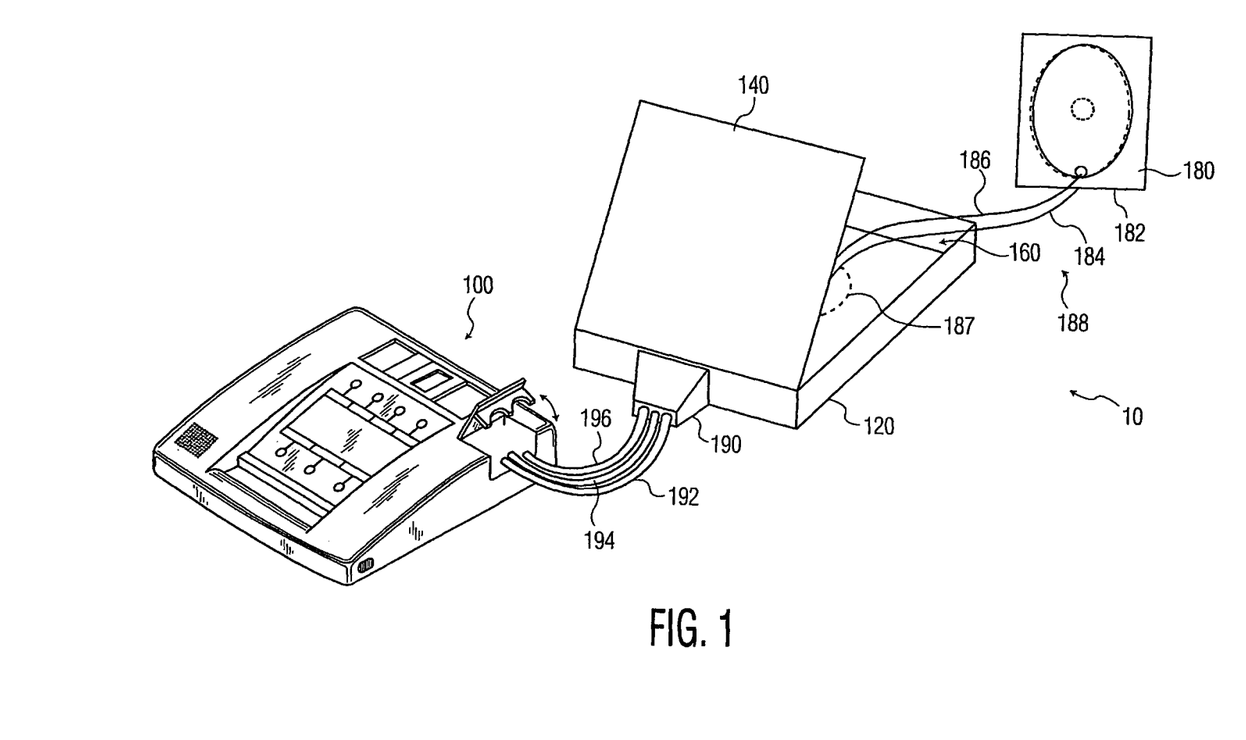
FIG. 1 is a perspective view of a defibrillation system according to the present invention.

FIG. 1 portrays an exemplary defibrillation system 19 of the present invention including a defibrillator 100 and a rigid cartridge 120 having a lid 140 shown in the open position. The cartridge 120 further has, defined in part by the lid 140, an electrode compartment 160 in which a pair of electrode pads 180, 182 (the second pad 182 being obscured by the visible one 180) may be stored. The pads 180, 182 have respective lead wires 184, 186 and typically each have on one surface a skin-adhesive, electrically conductive layer such as hydrogel, the hydrogel layers sandwiching an electrically non-conductive release layer. Openings may be provided in the release layer, as discussed in the '478 publication, to provide a pathway for the flow of electric current between the electrode pads 180, 182. An electrical conductor, such as metal foil, serving as one plate 187 of a capacitor is embedded in the bottom of the cartridge 120. The electrode pads 180, 182 together with their lead wires 184, 186 comprise the other plate 188 of the capacitor. Between the plates 187, 188 may be a dielectric material, air or free space to space the two capacitor plates apart and thereby form a capacitor. The lead wires 184, 186 are electrically connected by an electrical interface 190 to respective cables 192, 194, 196, that in turn, plug into the defibrillator 100 or other medical device.

The above implementation is merely exemplary. The defibrillator 100 shown is portable and has its own power pack, although other types of defibrillators may be employed, such as those that draw power from a wall outlet. Also, although a cartridge 120 is shown to be separate from the defibrillator 100, it is understood that they may be integrated, with the cartridge being implemented as a "well" of the defibrillator. In addition, the plate 187 need not necessarily be embedded within the bottom of the cartridge 120. It may, instead be mounted under the cartridge or in another position as long as it is disposed within the proximity of the electrode pads 180, 182.

Figure 2:
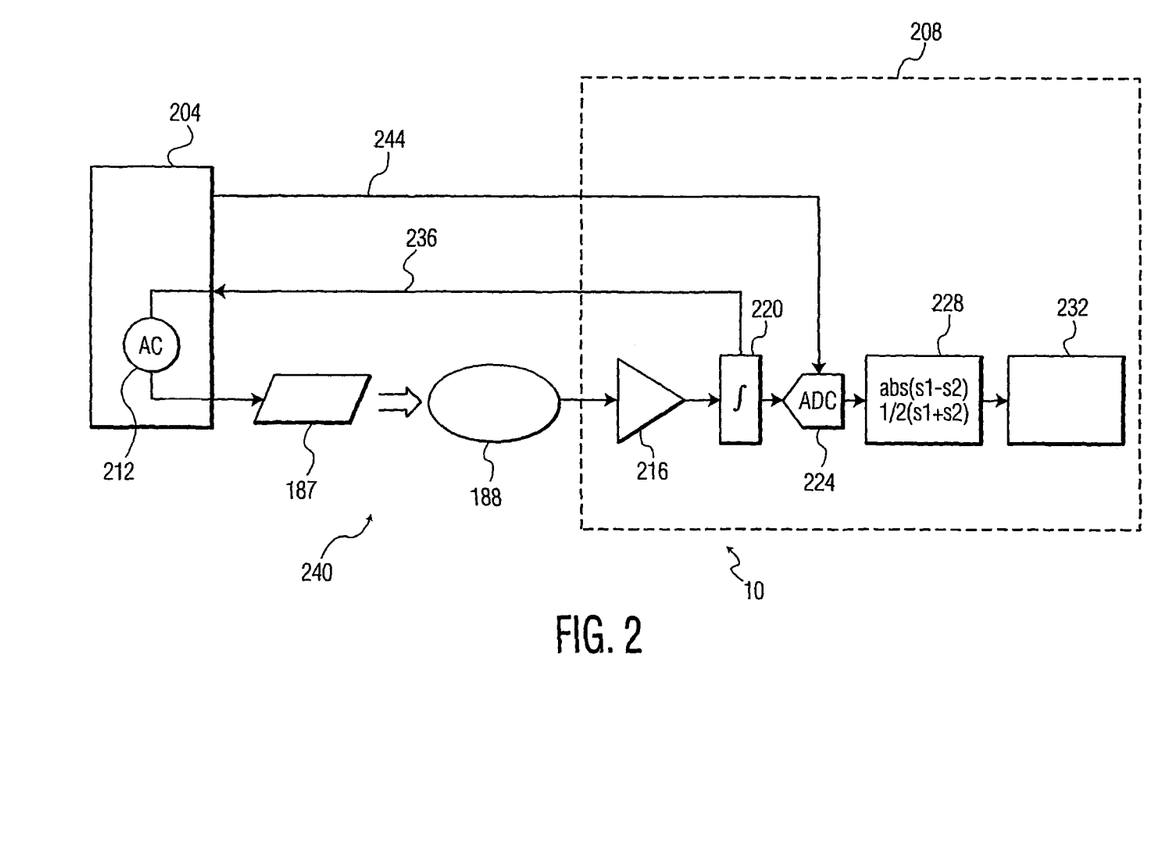
FIG. 2 is a functional block diagram of components within the defibrillation system according to the present invention and depicted in FIG. 1.

FIG. 2 is a functional block diagram that depicts, by way of example, components within the defibrillation system 10 according to the present invention. The defibrillator 100 includes a frequency shift key (FSK) generator 204 and an electrode deployment detector 208.

The FSK generator 204 provides an AC source 212 whose alternating frequency is periodically shifted in a time division manner among multiple values or "dither frequencies.". Dither frequencies used in one implementation are 24.390 KHz for the low frequency and 142.857 KHz for the high frequency. Alternation between the frequencies occurs every 125 ms. The generated signal is a square wave with a 50% duty cycle. All of the foregoing specifications are provided by way of example. For instance, other dither frequencies and/or more than two frequencies may be utilized. Frequency and duty cycle may be selectable by the user or programmed to vary in accordance with an internal table.

Included within the electrode deployment detector 208 are a voltage rectifier 216, and voltage-integrator 220, and analog-to-digital converter 124, a statistics generator 228 and a user prompt circuit 232. An AC circuit 236 comprised of the AC source 212, the plate 187, the pads and wires 188, the rectifier 216 and the integrator 220 alternates current in both the counterclockwise (as shown by the arrows) and clockwise directions across a capacitor 240 defined by the plates 187, 188.

The function of the AC circuit 236 is to afford detection of when the user manipulates and/or removes the pads and wires 188, so that the defibrillation system 10 can then advance to a prompt that guides the user in applying the electrode pads 180, 182 to the patient. As the distance between the plates 187, 188 increases, due to the user's handling/removal of the pads and wires 188, the capacitance of the capacitor 240 drops in accordance with the formula $C=KA/d$, where $C$, $K$, $A$ and d represent, respectively, capacitance, the dielectric constant, area of a plate 187, 188 and distance between the plates 187, 188. This formula provides an approximation since the pads and wires 188 are considered, for example, to have a "surface area" in correspondence with the surface area of the plate 187. As the capacitance drops upon removal of the pads 180, 182 or handling that deviates the respective "surfaces" from parallel, capacitive reactance rises according to the formula $X=1/(j\omega C)$, where X, w and C are, respectively, capacitive reactance, frequency (in radians per second) and capacitance. Impedance Z, which may be decomposed or represented as R+X where R represents resistance, therefore also rises in magnitude. The voltage drop across the capacitor 240 consequently rises according to the formula V=IZ, where I represents the current flowing across the capacitor. The increased voltage drop across the capacitor 240 is offset by a decreased voltage at the output of the integrator 220. This, decrease is realized for each of the voltage levels for respective dither frequencies, each frequency generating corresponding-capacitive reactance and therefore a respective voltage level.

The use of more than one frequency allows frequency-dependent effects to be detected. That is, a rise in impedance may be detected due to a rise in capacitive reactance or resistance. If it is capacitive reactance that is rising, this indicates a decrease in capacitance and therefore handling/removal of the pads 180, 182. On the other hand, a rise in resistance would not indicate such an event and might instead signal a system fault condition. To detect whether it is capacitive reactance or resistance that is rising, the invention dithers between two different frequencies. That is, since capacitance is multiplied by frequency in calculating capacitive reactance, a change in capacitance produces a greater change in capacitive reactance for one of the dither frequencies than for the other dither frequency and therefore a greater impedance change for one than for the other. By contrast, a change in resistance would affect the impedance for both frequencies similarly. Accordingly, a rise in capacitance due to removal/handling of the pads 180, 182 is more reliably detected through the use of two frequencies rather than one. In addition, the principles of the invention may be applied in training users to place the pads on the exterior of a training mannequin at the correct, unmarked locations that are responsive to electrical elements proximally embedded within the mannequin that normally create capacitive effects that are distinguished through the use of dithering frequencies.

During the period of each voltage level of the respective dither frequency, and preferably toward the end of the period to allow for settling of voltage at the integrator output, the FSK generator issues a start conversion command by means of a link 244 to the ADC 224. The ADC 224 then creates digital samples from the integrator output, from which the statistics generator 228 generates statistics. In the implementation shown, with two dither frequencies, corresponding voltage levels S1 and S2 are sampled. From these samples, the statistics generator 228 calculates two statistics, one representing the absolute value of the difference between S1 and S2 and the other representing the average of S1 and S2.

Both of the statistics decrease as the pads 180, 182 are removed. If however, the absolute difference statistic does not decrease significantly in comparison to the sum statistic, it is likely a resistive effect rather than any removal or handling of the pads 180, 182 that is responsible. The further apart the dither frequencies are spaced, the more marked is the difference between the reactions of the two statistics. Yet, a practical spacing breadth may be limited by the usable limits of the hardware.

The user prompt circuit compares the statistics, and if their change indicates the handling or removal of the pads 180, 182, advances the user prompt sequence to a prompt that guides the user in placing the pads 180, 182 correctly onto the patient.

Figure 3:
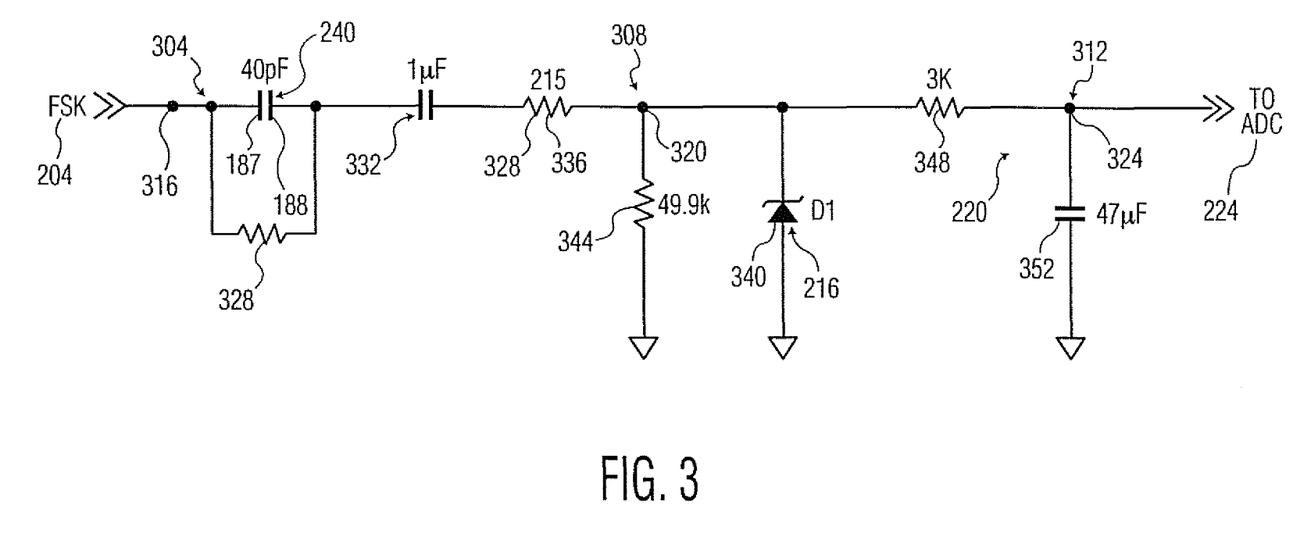
FIG. 3 is a circuit diagram with associated waveforms according to the present invention.
Figure 3A:
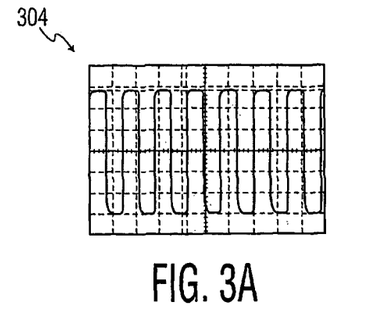
Figure 3B:
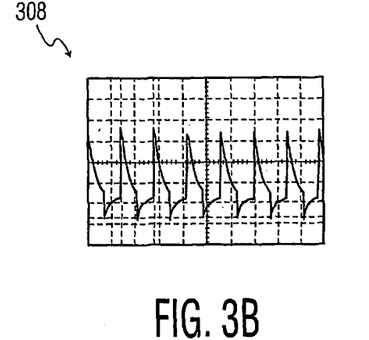
Figure 3C:
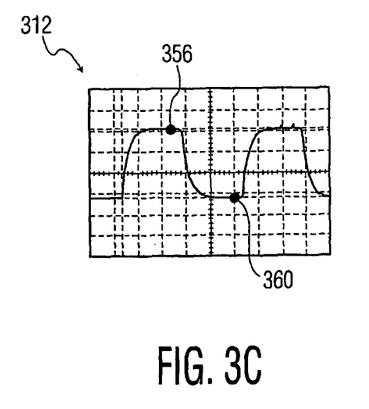

FIG. 3 is a diagram of the AC circuit 236 annotated with voltage waveforms 304, 308, 312 at respective measurement points 316, 320, 324 in the circuit. Waveforms 304 and 308 are shown at one FSK frequency for simplicity. Waveform 312 demonstrates the demodulated signal for both FSK frequencies. As shown in waveform 304, a square wave varying between 0 and +3 volts from the FSK generator 204 is applied across the capacitor 240 which has a capacitance of 40 Pico farads (pF), i.e., $4\times10^{-11}$ farads and which resides in parallel with a resistor 328. Although the exemplary value is 40 pF, the capacitance may be, for example, 10 pF, but is preferably very small, and, likewise, the resistance 328 is assumed to be very large. A blocking capacitor 332 has sufficient capacitance so as not to contribute any significant voltage drop, and therefore can be considered "out of the circuit." The blocking capacitor eliminates effects caused by half-cell reactions inherent in the chemistry of electrodes in contact. These effects are especially realized for pads on a release liner, e.g. with openings for mutual electrical contact by means of the hydrogel, and vary over temperature and time. The blocking capacitor 332 also reduces low frequency noise effects due to pad manipulation and half-cell voltage drift. A low resistance 336 is assumed in, for example, the lead wires 184, 186, which likewise contributes little to voltage drop. The rectifier 216 is implemented with a Schottky detector diode, which has a small forward voltage that clamps current across the large-resistance parallel resistor 344. Voltage is significantly rectified, as seen from waveform 308. The integrator 220 is implemented as a low-pass filter (LPF) with a resistor 348 and a capacitor 352 whose resistance and capacitance are sufficiently large to effectively integrate to steady voltage levels. These levels are shown by the dots 356, 360 on waveform 312, and correspond to sample S1 of one dither frequency and sample S2 of the other dither frequency, respectively.

Figure 4:
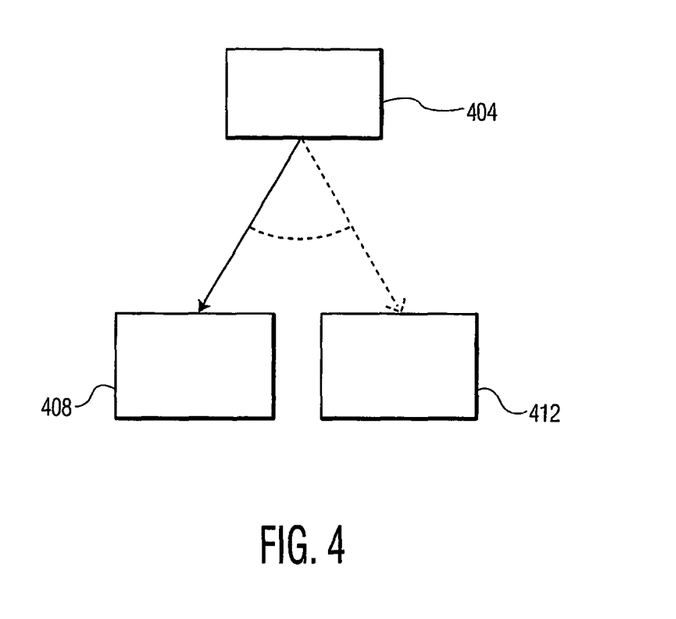
FIG. 4 is a conceptual block diagram of a joint implementation of pads-to-plate and pad-to-pad impedance monitoring according to the present invention.

FIG. 4 is a conceptual block diagram of a joint implementation of pads-to-plate and pad-to-pad impedance monitoring according to the present invention. The pads-to-plate monitoring of impedance from pads and wires 188 to plate 187 has been described above. As also mentioned above, the '674 application detects handling and/or removal of electrode pads based on detected variation in the pad-to-pad impedance, the electrodes in each pad being in mutual electrical connection by means of a conductive medium such as hydrogel. The pads-to-plate configuration would not require the mutual electrical connection, i.e., pads-to-plate sensing can be accomplished based on capacitance with a liner that does not have a conduction hole. However, providing the '674 electrical connection in the joint implementation affords detection even if the pads are manipulated or disturbed while in the well in a way that does not significantly affect capacitance. Complementarily, and as noted above, the pads-to-plate design will detect slower or gentler removal of the pads. The joint implementation therefore enjoys the advantages of both modes of operation, the pad-to-pad mode and the pads-to-plate mode.

The two modes of operation require different circuits to the pads 180, 182. In particular, for pad-to-pad impedance, a circuit is established that provides an electrical path up one of the lead wires 184, 186, across the pads 180, 182 and the intervening hydrogel, and down the other of the lead wires 184, 186. By contrast, the pads-to-plate impedance configuration creates electrical flow through the lead wires 184, 186 that concurrently runs in the same direction at any given time. In a time division manner, a time division multiplexer 404 alternates between two modes, one that monitors plate-to-pad impedance 408 and the other which monitors pad-to-pad impedance 412.

In mode 408, the FSK signal is split onto the cables 192, 194 for routing in parallel on the lead wires 184, 186, with the cable 196 then providing the return path, and a reverse path is followed when the current alternates. In mode 412, by contrast, one of the cables 192, 194 provides the forward current path and the other of the cables 192, 194 provides the return path. Optionally, the same AC source 212 can drive both modes if a third shift key is added for pad-to-pad current and the AC source terminals are shifted between circuits for the corresponding modes.

Mode 408 operates based on a changing voltage drop across a complex-impedance-generating element 240, the changing occurring as a result of expanding the element in handling or removing the element. The same principle can be extended in an inductive, rather than capacitive, configuration. The lead wires 184, 186 can be shaped in a coil when in the package 120, a coil sensitive to magnetic fields, i.e. an inductive coil. Expanding the coil, in handling/removing it and the pads 180, 182, the coil and pads together constituting the element 240, changes the voltage drop in an AC circuit 236 which is reconfigured to have, as in the 412 mode, a forward route up one of the wires 184, 186 and a return route along the other wire 184, 186, the plate 187 being removed from the circuit. Due to this forward and return routing, the cable 196 is no longer needed. Optionally, the same AC source 212 can drive both this inductive mode, and the 408 mode on the third shift key, for advantageously realizing the advantages of both modes on a reduced hardware implementation.

As has been demonstrated above, handling or removal of a pair of defibrillator electrode pads from their package is detected in order to effectively time the issuance of prompts to guide the user. The minimal hardware required for implementation provides a low-cost solution.

It is within the intended scope of the invention that features of the various above embodiments may be combined. For example, although FIG. 2 shows the plate 187 as the transmitter of the modulated signal and the pads and wires 188 as the receiver, the plate 187 may be implemented as the receiver with the pads and wires 188 as the transmitter.

While there have been shown and desorbed what are considered to be preferred embodiments of the invention, it will, of course be understood that various modifications and changes in form or detail could readily be made without departing from the spirit of the invention. It is therefore intended that the invention be not limited to the exact-forms described and illustrated, but should be constructed to cover all modifications that may fall within the scope of the appended claims.

What is claimed is:

1. A defibrillator apparatus comprising:
    an electrode with attached lead wire;
    an electrode compartment with an attached conductor;
    a source of alternating current; and
    an electrode deployment detector configured for:
        monitoring a magnitude of an electrical characteristic measured from an electrical circuit having from said source an alternating electric current path that includes said electrode with attached lead wire, said conductor, and a space or other electrical insulator intervening between said conductor and said electrode with attached lead wire, said compartment conductor being disposed in proximity of said electrode with attached lead wire to create capacitance in said electrical circuit; and
        identifying, based on a change of said magnitude, an occurrence of at least one of handling of said electrode with attached lead wire and removing of said electrode with attached lead wire from the compartment.

2. The apparatus of claim 1, wherein said electrical circuit is configured so that said magnitude varies with said capacitance.

3. The apparatus of claim 1, wherein said electrical circuit includes an integrator in series with said capacitance.

4. The apparatus of claim 3, wherein said electrical circuit further includes a rectifier for rectifying input voltage to the integrator.

5. The apparatus of claim 1, wherein said source periodically shifts between different frequencies of alteration.

6. The apparatus of claim 5, wherein said electrical circuit is configured so that said magnitude varies with said capacitance; and
    wherein said electrode deployment detector is configured to perform said identifying based on at least one of a sum and a difference between measurements of said magnitude that correspond to respective ones of said frequencies.

7. The apparatus of claim 1, wherein the alternating electric current path further includes another electrode and attached lead wire.

8. The apparatus of claim 7, wherein the alternating electric current path further comprises an electrically conductive medium disposed between the electrodes that provides a pathway for flow of electric current from one of the lead wires to the other by means of the electrodes and said medium.

9. The apparatus of claim 8, wherein activation of a source for the electric current from one of the lead wires to the other and activation of said source of alternating current are alternated in a time division manner.

10. The apparatus of claim 1, comprising a defibrillator that is configured to issue a sequence of user prompts and to advance from a particular one of the user prompts to a next one of the user prompts upon said identifying.

11. A method of detecting when a defibrillator electrode has been handled or removed from a storage compartment comprising the steps of:
    monitoring a magnitude of an electrical characteristic measured from an electrical circuit having from an alternating current source an alternating electric current path that includes an electrode with attached lead wire, a conductor attached to the storage compartment, and a space or other electrical insulator intervening between said conductor and said electrode with attached lead wire, said conductor being disposed in proximity of said electrode with attached lead wire when the electrode is stored in the compartment to create capacitance in said electrical circuit; and
    identifying, based on said magnitude, an occurrence of at least one of handling of said electrode with attached lead wire and removing said electrode with attached lead wire from the storage compartment.

12. The method of claim 11, wherein said electrical circuit is configured so that said magnitude varies with said capacitance.

13. The method of claim 11, wherein monitoring further comprises monitoring a magnitude of an electrical characteristic measured from the electrical circuit which includes an integrator in series with said capacitance.

14. The method of claim 13, wherein monitoring further comprises monitoring a magnitude of an electrical characteristic measured from the electrical circuit which further includes a rectifier for rectifying input voltage to the integrator.

15. The method of claim 11, wherein said source periodically shifts between different frequencies of alternation.

16. The method of claim 15, wherein said electrical circuit is configured so that said magnitude varies with said capacitance, and wherein the identifying step performs said identifying based on at least one of a sum and a difference between measurements of said magnitude that correspond to respective ones of said frequencies.

17. The method of claim 11, wherein monitoring further comprises monitoring a magnitude of an electrical characteristic measured from the electrical circuit having said alternating current path which further includes another electrode and attached lead wire.

18. The method of claim 17, wherein monitoring further comprises monitoring a magnitude of an electrical characteristic measured from the electrical circuit having said alternating current path which further comprises an electrically conductive medium disposed between the electrodes that provides a pathway for flow of electric current from one of the lead wires to the other by means of the electrodes and said medium.

19. The method of claim 18, wherein monitoring further comprises activating a source for the electric current from one of the lead wires to the other in a time division manner with the activation of said source of alternating current.

20. The method of claim 11, further comprising the step of issuing a sequence of user prompts, the issuing step including the step of advancing from a particular one of the user prompts to a next one of the user prompts upon said identifying.

* * * * *